(12) United States Patent
Zaldivar

(10) Patent No.: US 11,311,372 B2
(45) Date of Patent: Apr. 26, 2022

(54) INTRAOCULAR LENS IMPLANT FOR THE CORRECTION OF VISION

(71) Applicant: Smartech LLC, Miami, FL (US)

(72) Inventor: Roger Zaldivar, Miami, FL (US)

(73) Assignee: Smartech LLC, Miami, FL (US)

( * ) Notice: Subject to any disclaimer, the term of this patent is extended or adjusted under 35 U.S.C. 154(b) by 279 days.

(21) Appl. No.: 16/255,940

(22) Filed: Jan. 24, 2019

(65) Prior Publication Data

US 2019/0151079 A1 May 23, 2019

Related U.S. Application Data

(63) Continuation of application No. 14/031,940, filed on Sep. 19, 2013, now abandoned.

(60) Provisional application No. 61/702,995, filed on Sep. 19, 2012.

(51) Int. Cl.
*A61F 2/16* (2006.01)

(52) U.S. Cl.
CPC .......... *A61F 2/1624* (2013.01); *A61F 2/1602* (2013.01); *A61F 2/1618* (2013.01); *A61F 2002/1681* (2013.01); *A61F 2210/0023* (2013.01); *A61F 2250/0004* (2013.01)

(58) Field of Classification Search
CPC .... A61F 2/1624; A61F 2/1602; A61F 2/1618; A61F 2/16; A61F 2/1613; A61F 2/1627; A61F 2/1629; A61F 2/1632; A61F 2/1635; A61F 2002/1681
See application file for complete search history.

(56) References Cited

U.S. PATENT DOCUMENTS

| | | | | |
|---|---|---|---|---|
| 3,558,369 A | * | 1/1971 | Wang et al. .......... | C22C 19/007 148/563 |
| 2007/0135915 A1 | * | 6/2007 | Klima .................... | A61F 2/1629 623/6.37 |
| 2010/0121444 A1 | * | 5/2010 | Ben Nun ............... | A61F 2/1635 623/6.34 |
| 2011/0288638 A1 | * | 11/2011 | Smiley .................. | A61F 2/1624 623/6.37 |
| 2012/0323320 A1 | * | 12/2012 | Simonov ............... | A61F 2/1624 623/6.22 |

FOREIGN PATENT DOCUMENTS

WO   WO-2010125596 A1  *  11/2010  .......... A61F 2/1613

OTHER PUBLICATIONS

Definition of the term "crinkle" provided by www.oed.com, Jul. 2, 2021.*

* cited by examiner

*Primary Examiner* — Sarah A Simpson
(74) *Attorney, Agent, or Firm* — Defillo & Assoicates, Inc.; Evelyn A Defillo

(57) ABSTRACT

Novel intraocular lenses comprising at least one haptic having a shape memory alloy with a transition temperature substantially higher than the human body temperature, the shape memory alloy being post-surgically, selectively adjustable with a laser beam.

5 Claims, 21 Drawing Sheets

INTRAOCULAR LENS IMPLANT FOR THE CORRECTION OF VISION

CROSS REFERENCE TO RELATED APPLICATIONS

This application is a continuation of application Ser. No. 14/031,940 filed Sep. 19, 2013, entitled, INTRAOCULAR LENS AND METHOD, the content of which is incorporated herein by reference, which claims the benefit of U.S. Provisional Application No. 61/702,995 filed Sep. 19, 2012, the entirety of which is hereby incorporated by reference.

FIELD OF THE INVENTION

This disclosure relates to intraocular lenses for the improvement and correction of vision.

BACKGROUND OF THE INVENTION

The human eye is susceptible to a number of problems that affect the quality of vision. For example, as the eye ages, there is a loss of the ability to focus on near objects, a disorder known as presbyopia. Presbyopia is typically linked to a loss of elasticity of the crystalline lens. Another age-related problem is cataract formation, i.e., a clouding of the crystalline lens. This causes scattering, diminishment or complete blockage of optical light.

Vision quality is also affected by nearsightedness— known as myopia—in which the crystalline lens focuses light in front of the retina instead of directly on the retina. FIG. 1 illustrates a normally functioning eye in which lens 4 focuses light on retina 10. In contrast, FIG. 2 illustrates a myopic eye wherein lens 4 focuses light at a point 100 in front of the retina 10. Because light is focused in front of the retina 10, far-away objects appear blurry. Likewise, vision quality can be affected by farsightedness-known as hyperopia-in which the crystalline lens focuses light behind the retina, as shown in FIG. 3. Farsightedness makes near objects appear blurry.

Yet another frequent eye problem is astigmatism. Astigmatism is an optical defect in which vision is blurred due to the inability of the optics of the eye to focus a point object into a sharp focused image on the retina that may be due to an irregular or toric curvature of the cornea or lens.

PRIOR ART IOLS

Presbyopia, cataracts, myopia, astigmatism and a number of other eye-related problems can be dramatically improved or altogether corrected by surgical implantation of an intraocular lens (IOL). IOLs can be used to completely replace the natural lens, as shown in FIG. 4. Alternatively, a type of IOL, known as a phakic IOL (PIOLs), can be implanted in front of the natural lens (posterior chamber phakic IOLs), or in the anterior chamber (iris fixated phakic IOL and angle supported phakic IOL), thus altering the power of the entire eye. PIOLs are illustrated in FIGS. 5-6.

Presently available IOLs are formed from a flexible, plastic lens. In addition, each IOL has flexible, radial struts or wings-known as haptics-that secure the lens within the eye. This configuration allows a physician to collapse or roll the IOL into a compact shape for implantation, and then unroll and position the IOL within the eye.

IOL lenses have either a monofocal or multifocal refractive value or diopter. To achieve ideal vision, also known as emmetropia, a physician must properly calculate the appropriate refractive power and size particularly in phakic IOLs suitable for each eye.

DRAWBACKS OF PRIOR ART IOLS

While IOLs have drastically improved treatment of many eye problems, IOLs still have significant drawbacks.

One significant drawback to presently available IOLs relates to selection of the ideal diopter for the IOL for a particular eye. In particular, selection of an IOL having an incorrect diopter for a particular eye leads to post-surgical refractive residual error (myopia, hyperopia or astigmatism). In spite of recent improvements in ophthalmic devices and methods for diopter calculation, the resulting selected diopter is not ideal. Indeed, studies of lens replacement patients treated by an experienced ophthalmologist show that about 50% of patients are not entirely satisfied with the surgical outcome and likely need an optical correction to appropriately to further improve their vision.

Another drawback to presently available IOLs relates to misalignment of toric IOLs (astigmatism correction). In cases involving astigmatism, misalignment of the IOL may result in a residual astigmatism.

Another significant drawback to presently available IOLs occurs during cataract surgery. During cataract surgery, the cataract is removed from the sac that surrounds it, also called the capsular bag. The capsular bag remains in place because of the support provided by the zonule. The IOL is implanted most frequently inside the capsular bag in cataract surgery, as shown in FIG. 4. In some cases, the IOL is implanted outside the capsular bag, most frequently at the sulcus. The power of the IOL will depend in the final position inside the eye being stronger if it shifts anteriorly or weaker if it shifts posteriorly. This is known as the estimated lens position (ELP) and is the most difficult thing to predict during the calculation of the IOL and the main source of error.

Yet another significant drawback relates to the requirement that a PIOL be positioned precisely relative to the natural lens or the endothelium. PIOLs can be positioned either in the posterior or anterior chamber of any eye. For PIOLs implanted in the posterior chamber, shown in FIG. 5, the desired spacing (gauged as a type 2 vault) between the PIOL and the front of the natural lens ranges from about 500 to about 750 microns. As such, there is almost no margin of error. Positioning can be further complicated by the presence of cataracts and pupillary block. Where a posterior chamber PIOL is too close to the natural lens, even to the point of actual contact with the natural lens (vault of 1 and 0, respectively), the patient is prone to developing cataracts or other opacities. On the other hand, positioning a posterior chamber PIOL too far from the natural lens, (i.e., a vault of 3 or 4), can lead to compression of the iridocorneal angle, and in some cases to pupillary block and acute glaucoma. For lenses implanted in the anterior chamber, shown in FIG. 6, positioning and sizing of the PIOL is crucial. Decompensation of corneal endothelial cell loss, iris atrophy and cataract formation has been described related to this issue. This is the reason why, despite being optically a great solution for addressing the need to use glasses, the considerable number of complications related to PIOLs hinders its global acceptance.

Follow-up surgery is the only present solution to the previously mentioned drawbacks and complications with current IOLs. Surgical options related with residual refractive errors include laser in situ keratomileusis, photorefractive keratomileusis, limbar relaxing incisions, or complete surgical removal and replacement of the IOL or PIOL. Follow-up surgery, however, is extremely undesirable because it results in increased patient discomfort and recovery time, the possibility of further complications, and much higher costs. The sole non-surgical alternative—which is only available alternative in certain circumstances—is to wear glasses. However, even wearing glasses to solve a post-surgical IOL or PIOL problem is also extremely undesirable. Indeed, the desire to dispense with glasses may often be the very reason that a patient may have undergone the surgical procedure to begin with. Surgical options related to errors in sizing and positioning of phakic IOLs include their replacement, phaco surgery, and corneal transplant.

Accordingly, there is an unfulfilled need for an IOL or PIOL that resolves or improves upon one or more of the drawbacks and complications attributable to present IOLs and PIOLs.

SUMMARY OF THE INVENTION

One or more of the preceding drawbacks of currently available IOLs and PIOLs are improved and an advance is made in the art by a novel a phakic, pseudophakic, monofocal, or multifocal IOL. According to one aspect of the present invention, an IOL is provided that can be selectively repositioned, resized or otherwise adjusted non-invasively after implantation in a patient. According to another aspect of the present invention, a novel IOL is provided with haptics that can be repositioned, resized or otherwise adjusted non-invasively after implantation in a patient. According to another aspect of the present invention, a novel IOL is provided with a lens having a diopter that can be adjusted non-invasively after implantation in a patient.

According to another aspect of the present invention, a method is disclosed for repositioning, resizing or otherwise adjusting an IOL non-invasively.

One embodiment of an intraocular lens implant for the correction of vision may include an optical body with a default refractive power, and a haptic operably connected to the optical body, the haptic comprising at least one shape memory alloy having a segment with a transition temperature substantially higher than the body temperature of a human. The segment may be non-linear at temperatures below the transition temperature and substantially linear at temperatures above the transition temperature.

The optical body may include a monofocal region, or a multifocal region. The segment may be linear at temperatures below the transition temperature and non-linear at temperatures above the transition temperature. The embodiment of the intraocular lens implant may further include a second haptic operable connected to the optical body, the second haptic comprising a second shape memory alloy having a second segment with a transition temperature substantially higher than the body temperature of a human. The transition temperature may be between 50 degrees Celsius and 500 degrees Celsius.

In another embodiment of an intraocular lens implant for the correction vision, the intraocular lens implant may include an optical body with a default refractive power, and a haptic operably connected to the optical body, the haptic including an expansion zone and at least one shape memory bar provided in or proximate to the expansion zone, a segment of the memory bar having a transition temperature greater than 50 degrees Celsius, wherein the expansion zone of the haptic is deformable when the at least a portion of the memory bar has reached its transition temperature. The embodiment may further include an additional haptic connected to a side of the optical body opposing the haptic, the additional haptic including an expansion zone and at least one shape memory bar provided in or proximate to the expansion zone, a segment of the memory bar having a transition temperature greater than 50 degrees Celsius, and the expansion zone of the additional haptic is deformable when the at least a portion of the memory bar has reached its transition temperature. The haptic may include a plurality of shape memory bars provided in or proximate to the expansion zone of the haptic, and the additional haptic may include a plurality of shape memory bars provided in or proximate to the expansion zone of the additional haptic. The memory bars in either or both the haptic and the additional haptic may be composed of a shape memory alloy, the shape memory alloy comprising nickel titanium. The expansion zone may be crinkled.

An embodiment of the invention is a method for non-surgically adjusting the position of an implanted intraocular lens may include providing an intraocular lens implant for the correction of vision including an optical body with a default refractive power, a haptic operably connected to the optical body, the haptic comprising at least one shape memory alloy having a segment with a transition temperature substantially higher than the body temperature of a human, implanting the intraocular lens within the eye of a patient, post-surgically dilating the eye, providing an electromagnetic wave delivery means, delivering electromagnetic waves with the deliver means to a predetermined section of the segment until the segment reaches the transition temperature, whereby the haptic is deformed so as to exert a desired biasing force within the eye. The biasing force may secure, reposition, or adjust the intraocular lens implant within the eye. The biasing force may also align the intraocular lens implant to a desired position within the eye. The laser may be an argon laser.

Other characteristics and advantages of the invention will be discernible to the ordinarily skilled artisan when equipped with the teachings of the present disclosure. Certain objects and advantages of the present invention may be realized when the instrumentalities and combinations particularly pointed out in the appended claims are considered.

The foregoing and other objectives, features, and advantages of the invention will be more readily understood upon consideration of the following detailed description of the invention.

BRIEF DESCRIPTION OF THE DRAWINGS

The following numerical descriptors are employed in certain of FIGS. 1 to 21 to identify the various structural elements being represented: cornea (1); central iris (2a); peripheral iris (2b); posterior chamber (3a); anterior chamber (3b); natural lens (4); sulcus (5); ciliary zonule (6); area of the intraocular lens optic or optical body (107); proximal area of the haptic (108a); distal area of the haptic (108b); retina (10); memory alloy device shape (11).

DETAILED DESCRIPTION OF THE ILLUSTRATIVE EMBODIMENTS

The following detailed description and the appended drawings describe and illustrate exemplary embodiments of the invention solely for the purpose of enabling one of ordinary skill in the relevant art to make and use the invention. As such, the detailed description and illustration of these embodiments are purely exemplary in nature and are in no way intended to limit the scope of the invention, or its protection, in any manner. It should also be understood that the drawings may not be to scale and in certain instances details have been omitted, which are not necessary for an understanding of the present invention, such as conventional details of fabrication and assembly.

Definitions

As employed throughout the disclosure of the present invention, the following terms, unless otherwise indicated, shall be understood to have the following meanings.

As used herein, the term "emmetropia" refers to the ideal refractive state of the eye.

As used herein, the term "substantially emmetropic state" refers to refractive states of the eye that reasonably closely approximate the ideal refractive state of the eye including refractive states influenced by conditions of astigmatism, myopia and hyperopia (e.g., conditions with refractive states diverging from ideal). Typically, refractive states that are substantially emmetropic include states that diverge from the ideal in the range of from about 0 to about 10%. Alternatively, a substantially emmetropic state as used herein would provide vision acuity of at least about 90%, preferably of at least about 95%, more preferably of at least about 98% and still more preferably of at least about 99% of the same eye at emmotropia.

As used herein, the term "anterior chamber" refers to the part of the anterior cavity of the eye in front of the iris that contains the aqueous humor.

As used herein, the term "posterior chamber" refers to that part of the aqueous humor-containing space of the eyeball between the iris and the lens.

As used herein, the term "refractive power" refers to the degree to which a lens, mirror, or other optical system converges or diverges light.

As used herein, the term "shape memory alloy" refers to an alloy that "remembers" its original, cold-forged shape. When a shape-memory alloy is in its cold state, the metal can be bent or stretched and will hold those shapes until heated above the transition temperature. Upon heating, the shape changes to its original forged shape. When the metal cools again it will remain in the hot shape, until deformed again. One exemplary "shape memory alloy" is Nickel Titanium (NiTi), otherwise known as Nitinol.

Figure 7:
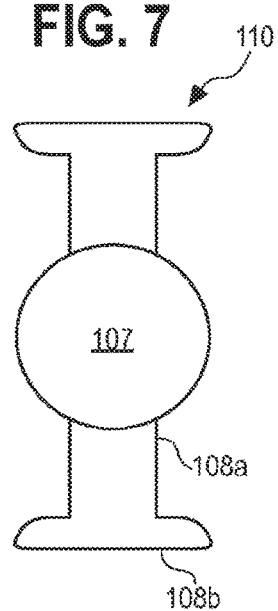
FIG. 7 is a front view of a type of intraocular lens useful in the present invention.
Figure 7A:
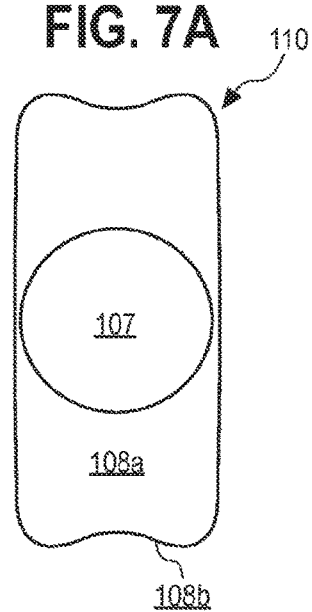
FIG. 7A is a front view of another type of intraocular lens useful in the present Invention.
Figure 7B:
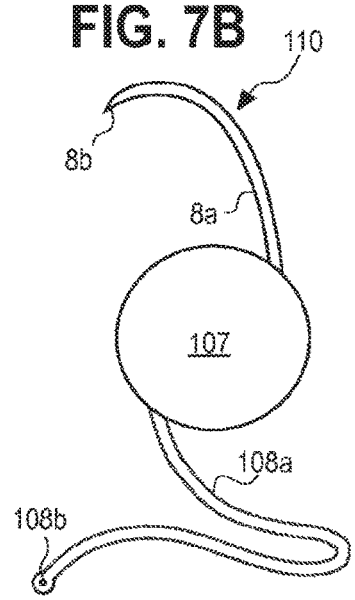
FIG. 7B is a front view of another type of intraocular lens useful in the present invention.
Figure 7C:
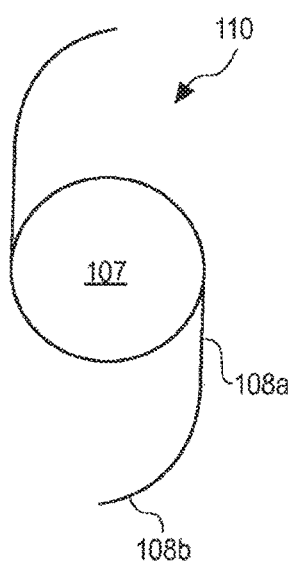
FIG. 7C is a front view of another type of intraocular lens useful in the present invention.
Figure 7D:
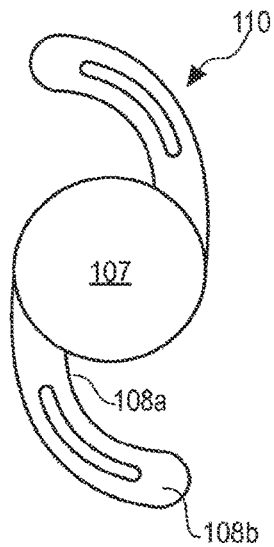
FIG. 7D is a front view of another type of intraocular lens useful in the present invention.
Figure 7E:
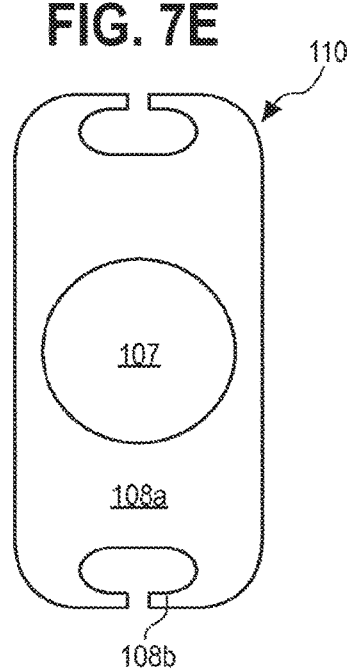
FIG. 7E is a front view of another type of intraocular lens useful in the present invention.
Figure 8:
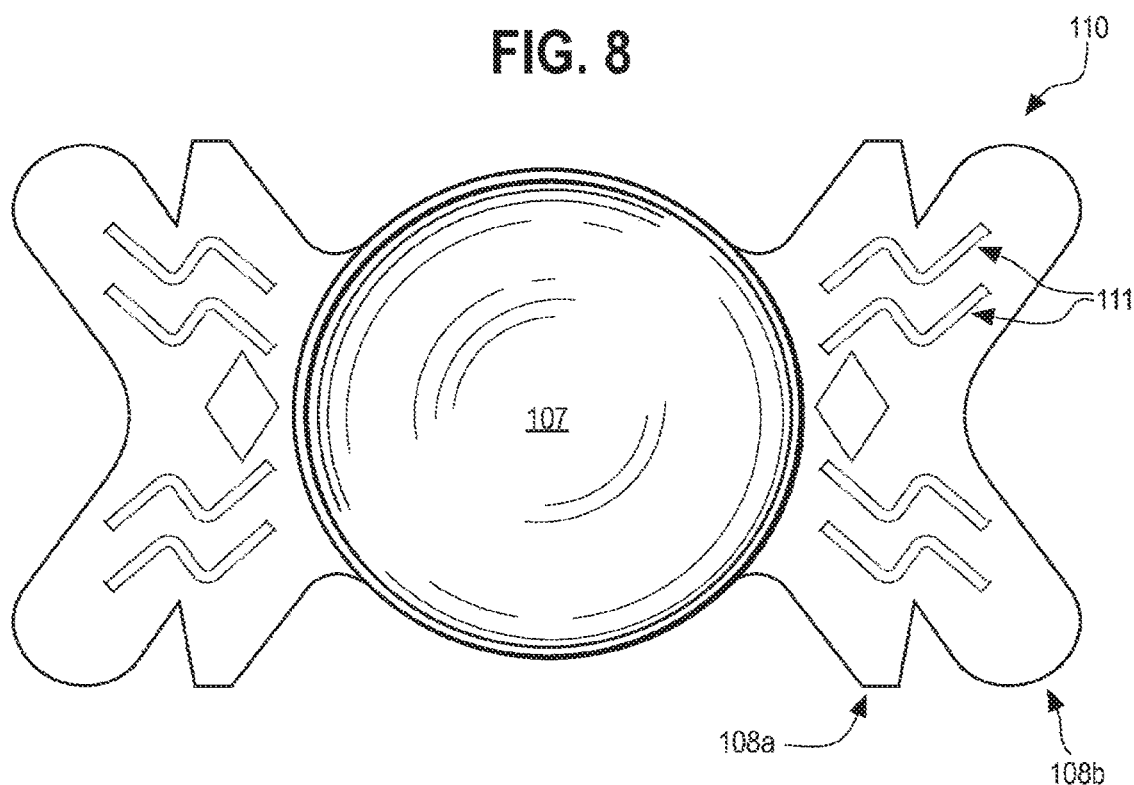
FIG. 8 is a front view of an embodiment of an intraocular lens with memory alloy and at least one lens haptic.
Figure 8A:
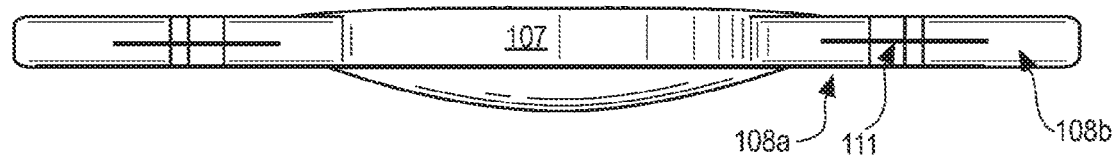
FIG. 8A is a side view of the intraocular lens of FIG. 8.
Figure 9:
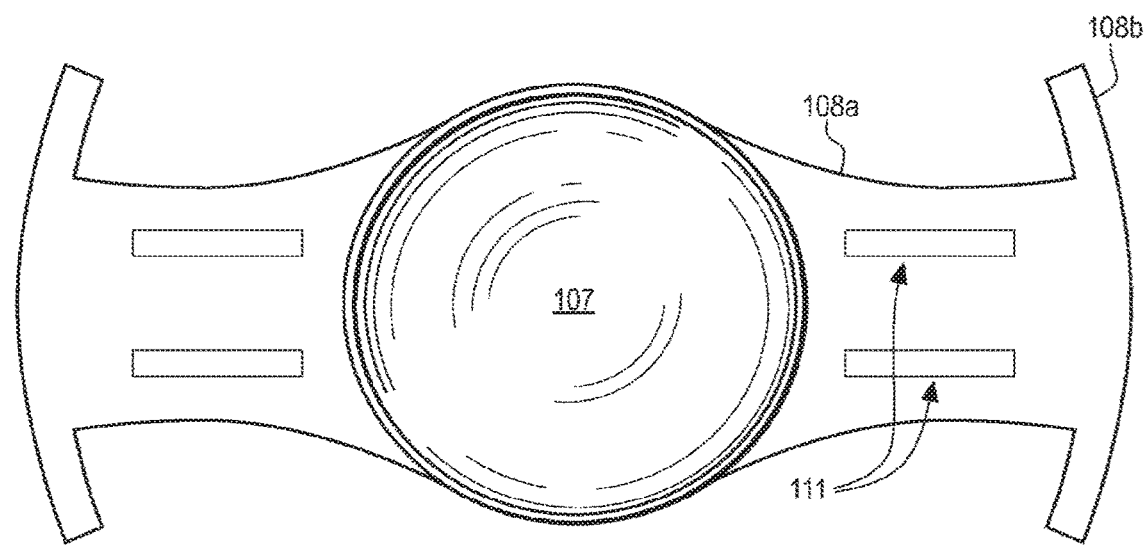
FIG. 9 is a front view of an embodiment of an intraocular lens with memory alloy and at least one lens haptic.
Figure 9A:
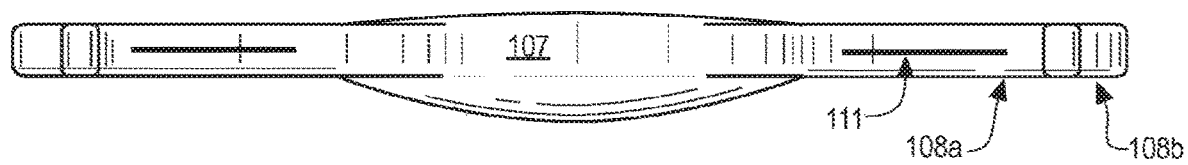
FIG. 9A is a side view of the intraocular lens of FIG. 9.
Figure 10:
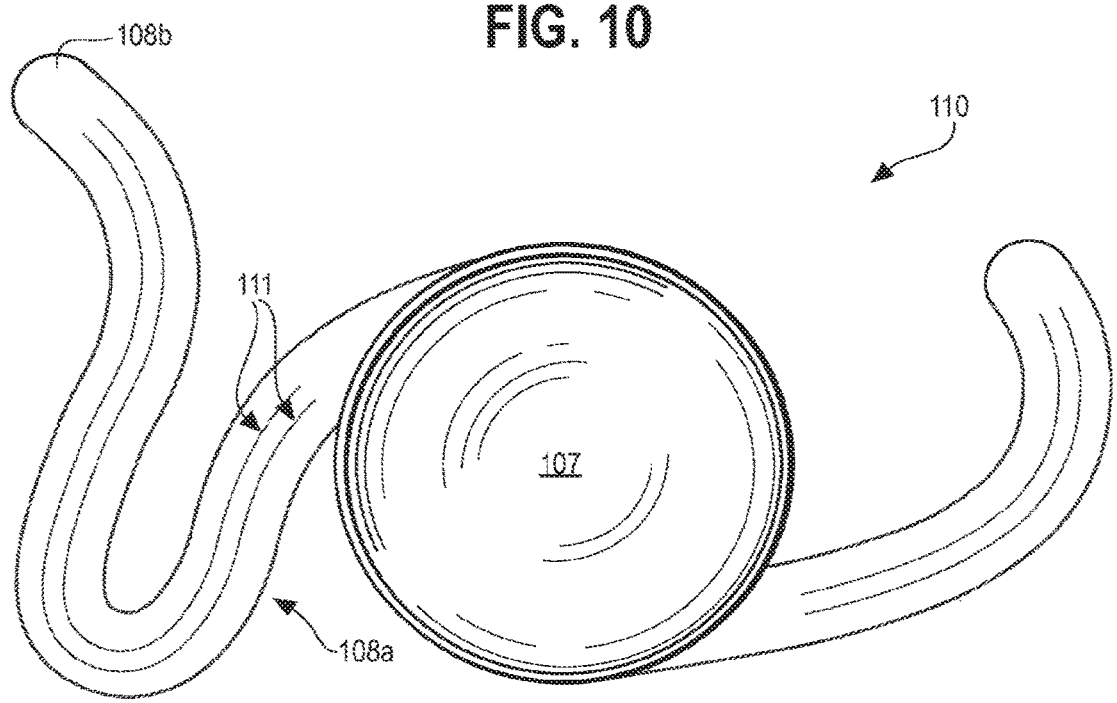
FIG. 10 is a front view of an embodiment of an intraocular lens with memory alloy and at least one lens haptic.
Figure 10A:
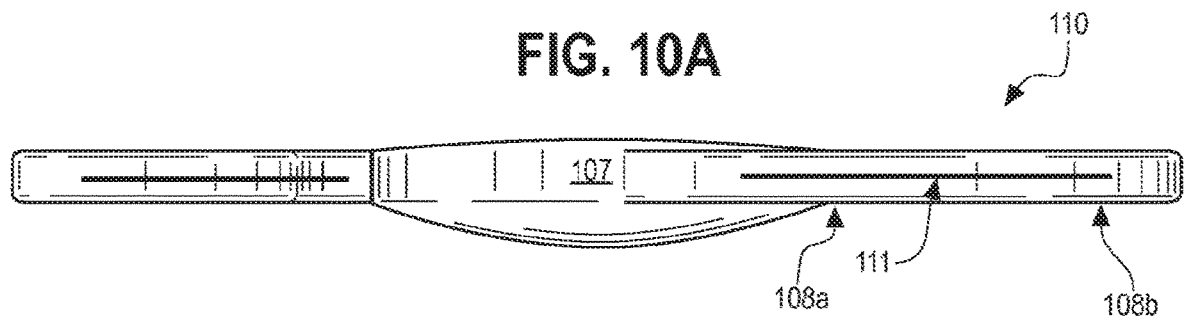
FIG. 10A is a side view of the intraocular lens of FIG. 10.
Figure 11:
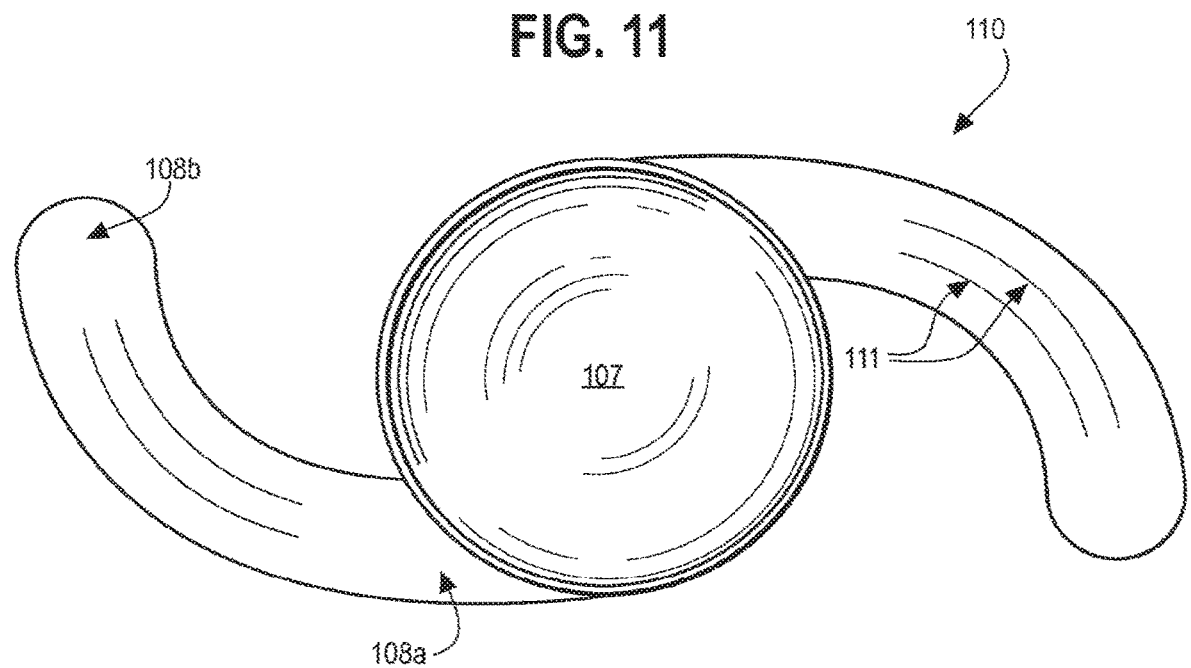
FIG. 11 is a front view of an embodiment of an intraocular lens with memory alloy and at least one lens haptic.
Figure 11A:
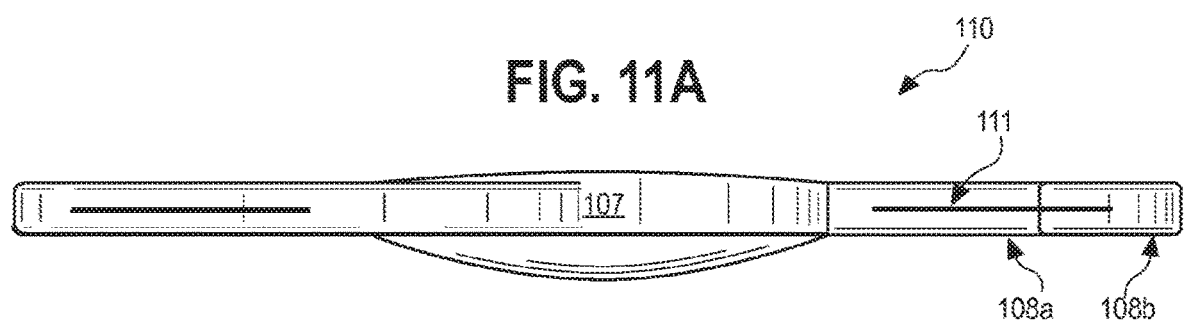
FIG. 11A is a side view of the intraocular lens of FIG. 11.

Referring to the drawings, FIGS. 7-21 illustrate various embodiments of an IOL 110, each of which generally includes a flexible optical body or lens 107 joined to haptics 108. FIG. 7 illustrates a number of embodiments of an IOL having a lens 107 with a default optical or refractive power. In addition, such IOLs have at least one haptic 108 with a proximate area 108a adjacent to the optical body 107, and a distal area 108b at the terminal end of the haptic. Haptic 108 may be formed entirely of a shape memory alloy. Alternatively, haptic 108 may be a flexible plastic material having integral shape memory bars 111.

Figure 12:
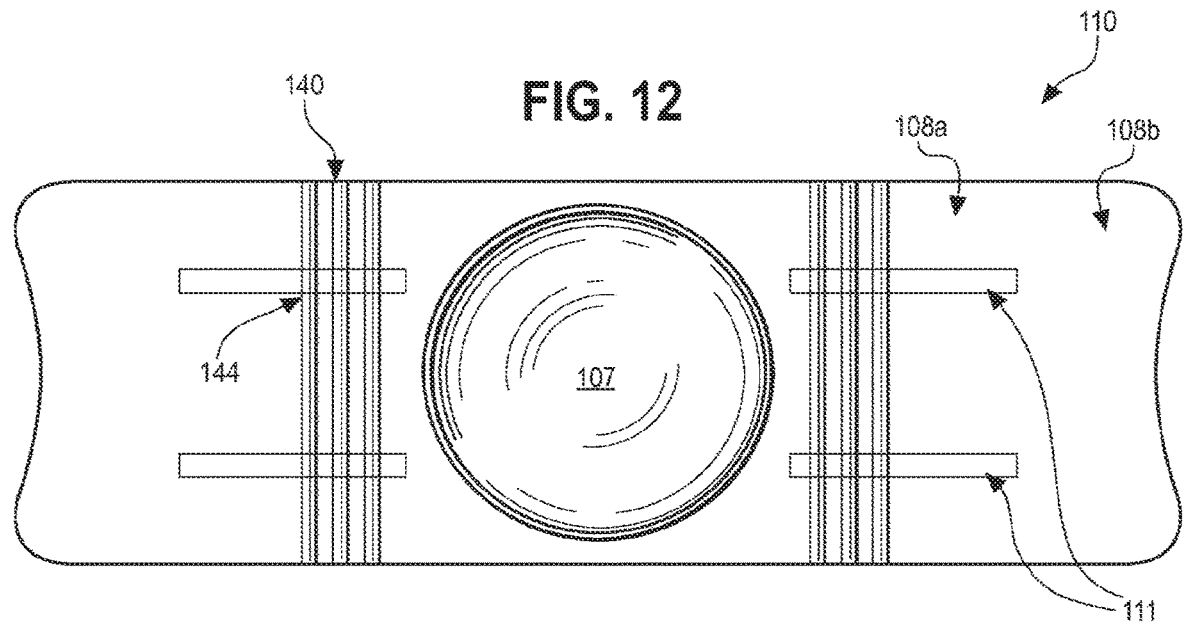
FIG. 12 is a front view of an embodiment of an intraocular lens with memory alloy and at least one lens haptic.
Figure 12A:
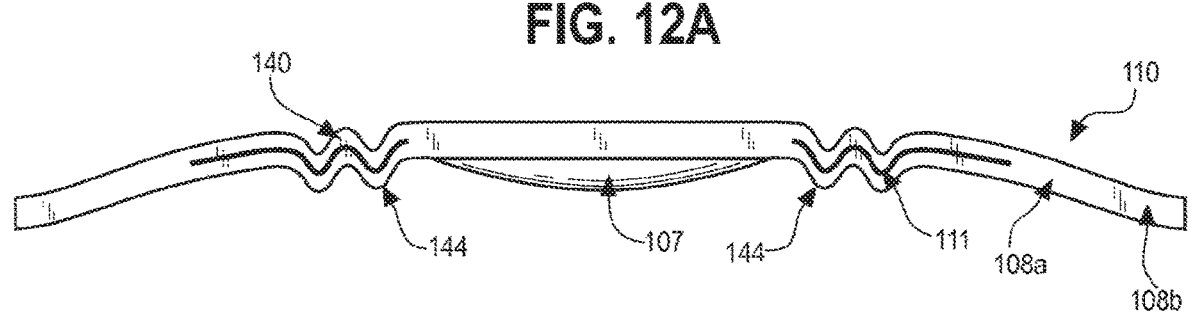
FIG. 12A is a side view of the intraocular lens of FIG. 12.
Figure 13:
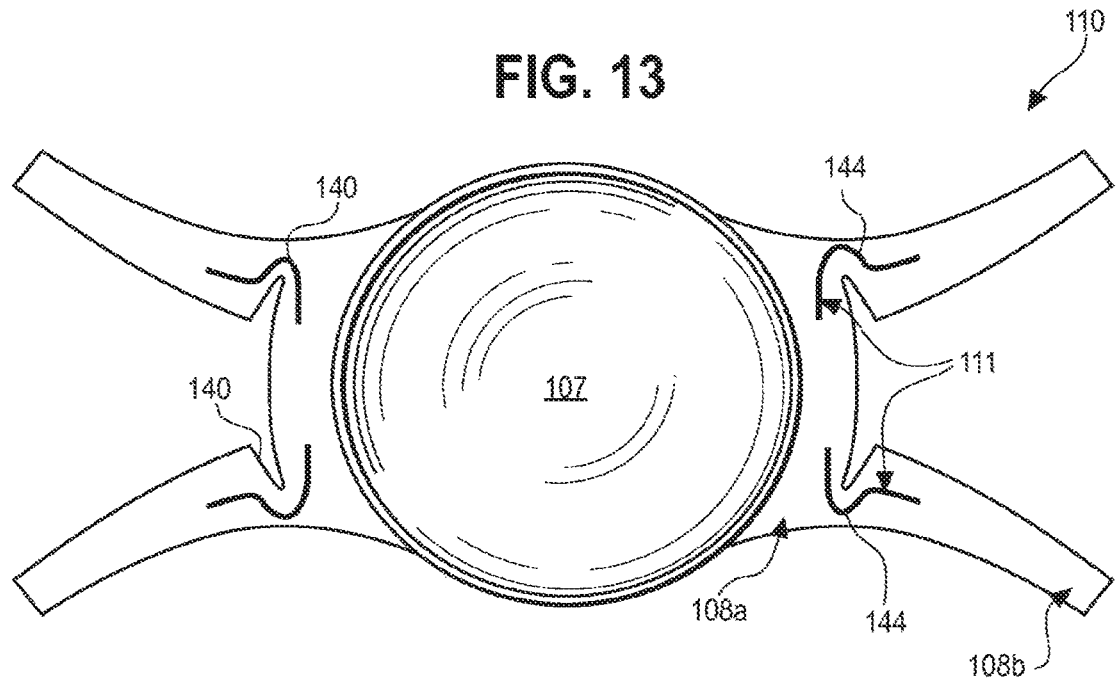
FIG. 13 is a front view of an embodiment of an intraocular lens with memory alloy and at least one lens haptic.
Figure 13A:
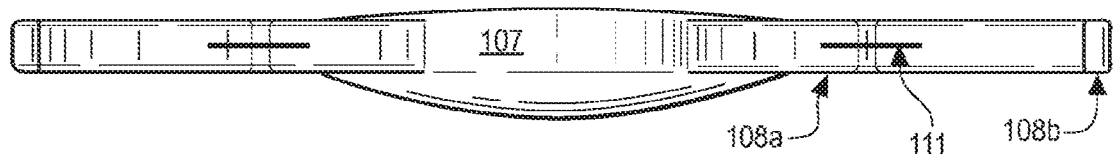
FIG. 13A is a side view of the intraocular lens of FIG. 13.
Figure 14:
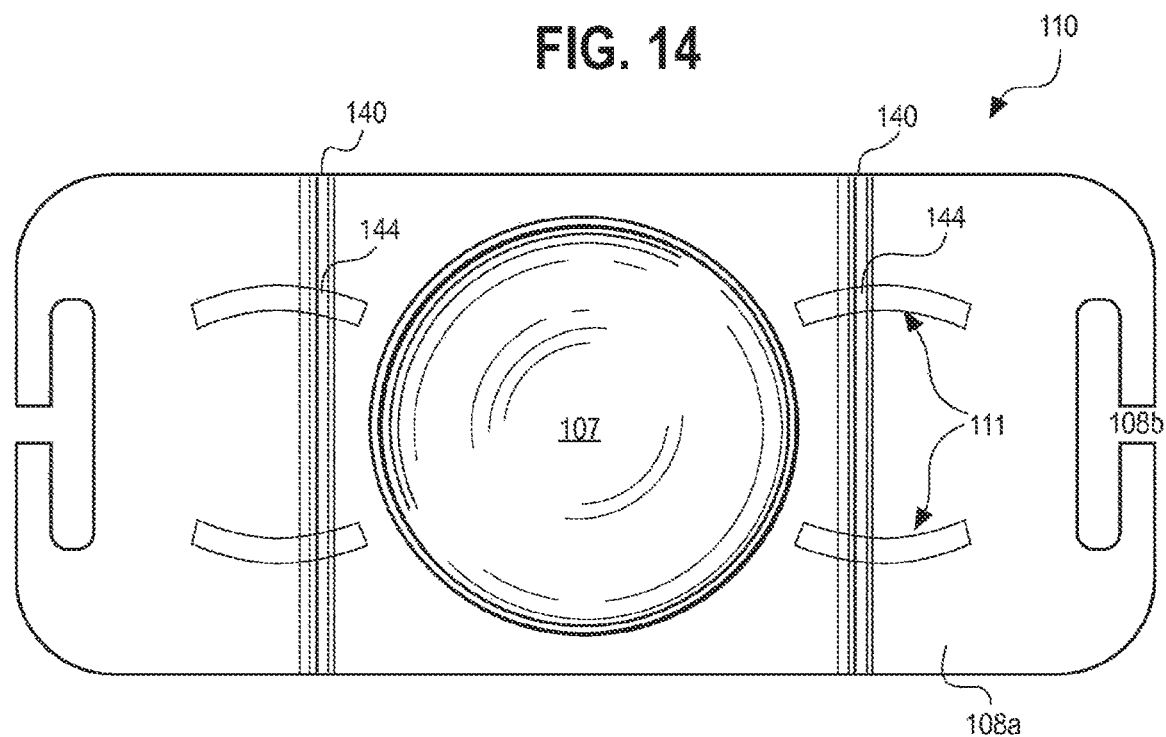
FIG. 14 is a front view of an embodiment of an intraocular lens with memory alloy and at least one lens haptic.
Figure 14A:
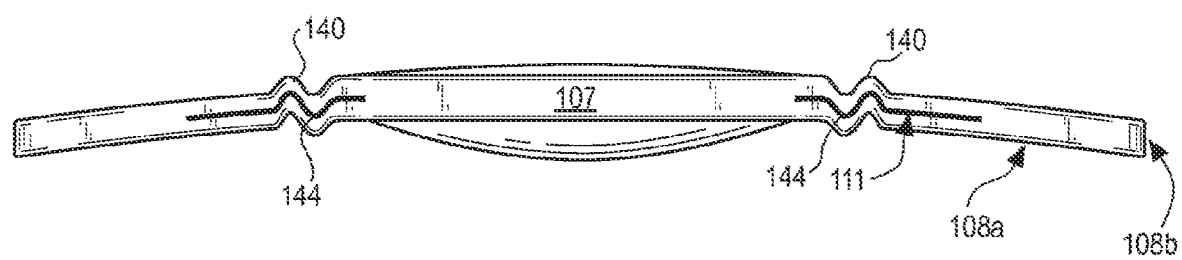
FIG. 14A is a side view of the intraocular lens of FIG. 14.

FIGS. 7 through 14 illustrate alternative designs of IOL 110 having haptic 108 and shape memory bars 111. As illustrated in FIG. 12, shape memory bars 111 are provided with one or more crinkled or bent portions 144 that coincide with the expansion zones 140. Such zones are configured to be heated to elongate, bend more, or even rotate about an axis of the haptic 108. Such zones are preferably identified or marked in such a manner that a physician can select one or more zones to heat in order to achieve a desired change in the position and shape of the haptic.

In one embodiment, shown in FIG. 12, IOL 110 is provided in an elongate, rectangular configuration having curvilinear corners, haptics 108, haptic expansion zones 140 and shape memory bar expansion zones 144. Each shape memory bar 111 and expansion zone 140 is configured to remain in a first, closed or retracted position before, during and after the procedure in which IOL 110 is implanted. If adjustment of the position, size, or shape of the IOL 110 is desired, a physician can apply focused, electromagnetic wave on predetermined locations of each shape memory bar 111 until the shape memory bar reaches the pre-set transition temperature and returns to its forged state. The physician can thus move IOL 110 toward or away from the retina, or bias the haptics against the surrounding tissues to reposition the lens radially within the eye, or even readjust the biasing force of the haptics to reduce unwanted bias against surrounding tissue or increase desired bias against surrounding tissue.

The stimulus with electromagnetic waves in a pre-determined designed area of the memory alloy shape induces a movement that is transferred to the proximal haptic bodies 108*a* and distal ends 108*b*, which changes the position, orientation, or intraocular lens shape, such as its curvature or vault, as desired. The nature and extent of the lens repositioning or adjusting is a function of the location of the shape memory alloy, the power of the irradiation, the time of irradiation. Lasers such as argon lasers are very useful in this regard for their ability to narrowly focus the beam of energy on a particular surface location of the alloy to bring about the desired adjustment or repositioning.

As will become apparent to one of ordinary skill in the art in view of this disclosure, numerous shape memory bars, and combinations thereof, can be used to provide for desired deformations and movements of IOL 110. More specifically, by heating different parts of the shape memory bars, a physician can, in a choreographed manner effect changes in the IOL 110 that better secure, realign, reposition or refocus an IOL in situ and without the need for surgery. Indeed, the physician can employ a laser to effect movement of IOL 110 in any number of directions, including, inter alia, radially, forward or backward, depending on the alloy, its low temperature shape and transition shape, as well as its location in the haptic.

Importantly, the transition temperature of the shape memory bars is set significantly higher than a human's normal body temperature range, and preferably higher than approximately 50 degrees Celsius. Otherwise, upon insertion into a patient, shape memory bars 111 would reach their transition temperature and cause the undesirable, uncontrolled return of the shape memory bars 111 to their original forged state. Such uncontrolled transition could displace the IOL 110 or cause other undesirable side effects.

Figure 1:
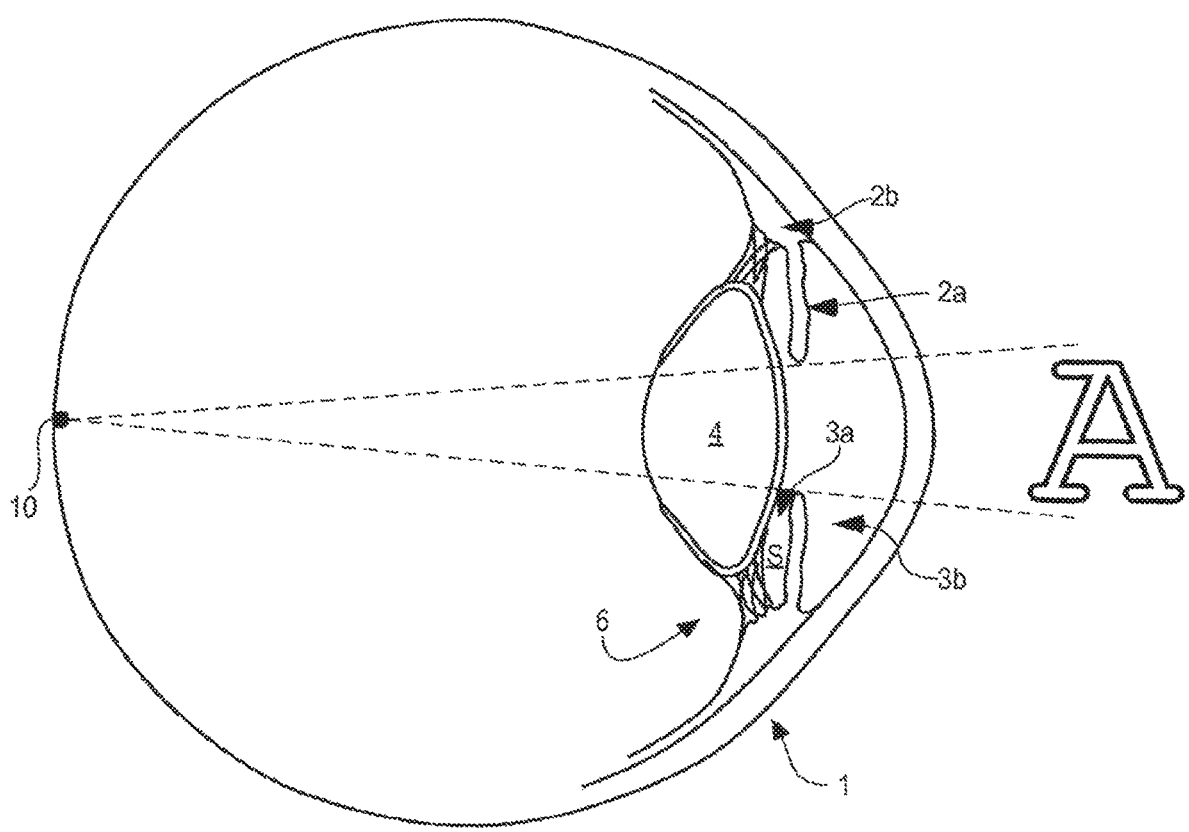
FIG. 1 is a cross-sectional side view of an eye and its main internal structures, demonstrating the proper focal point of the eye in the visual state of emmetropia.
Figure 2:
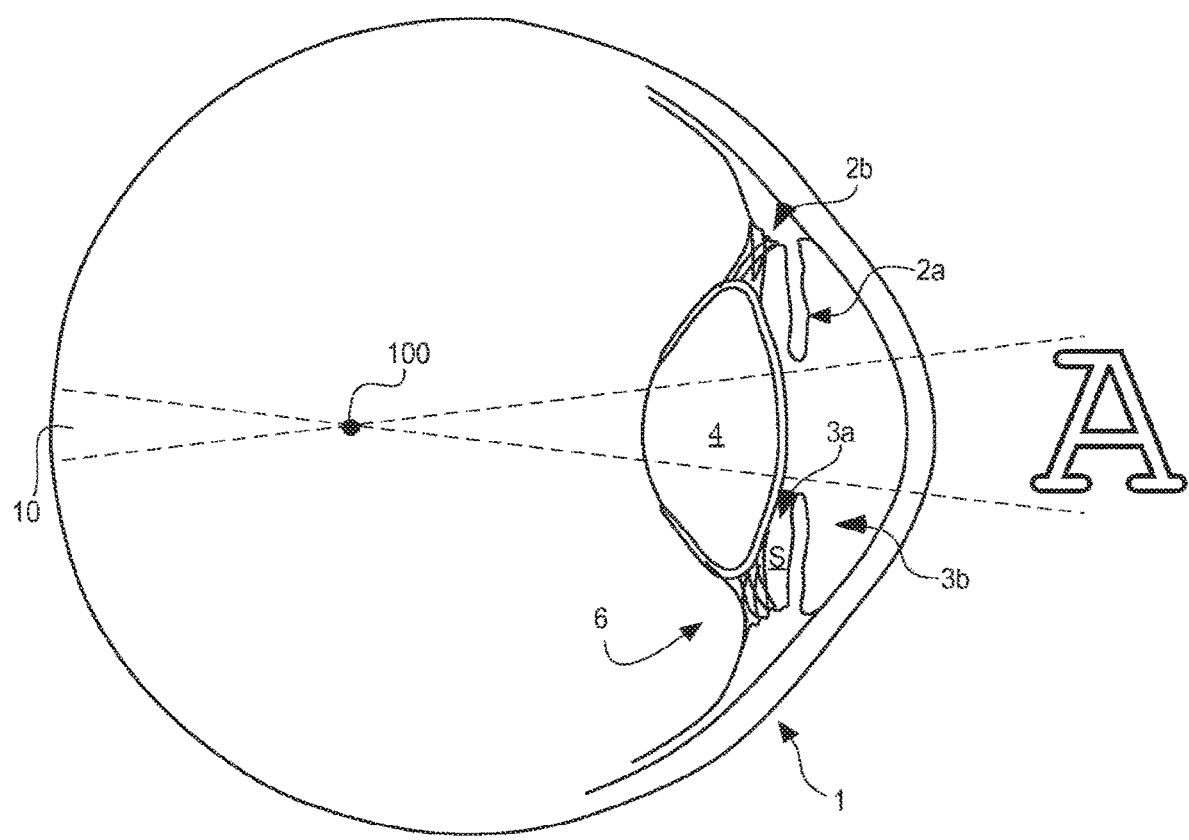
FIG. 2 is a cross-sectional side view of an eye and its main internal structures, demonstrating the forward (relative to optimum) focal point of the eye in the visual state of myopia.
Figure 3:
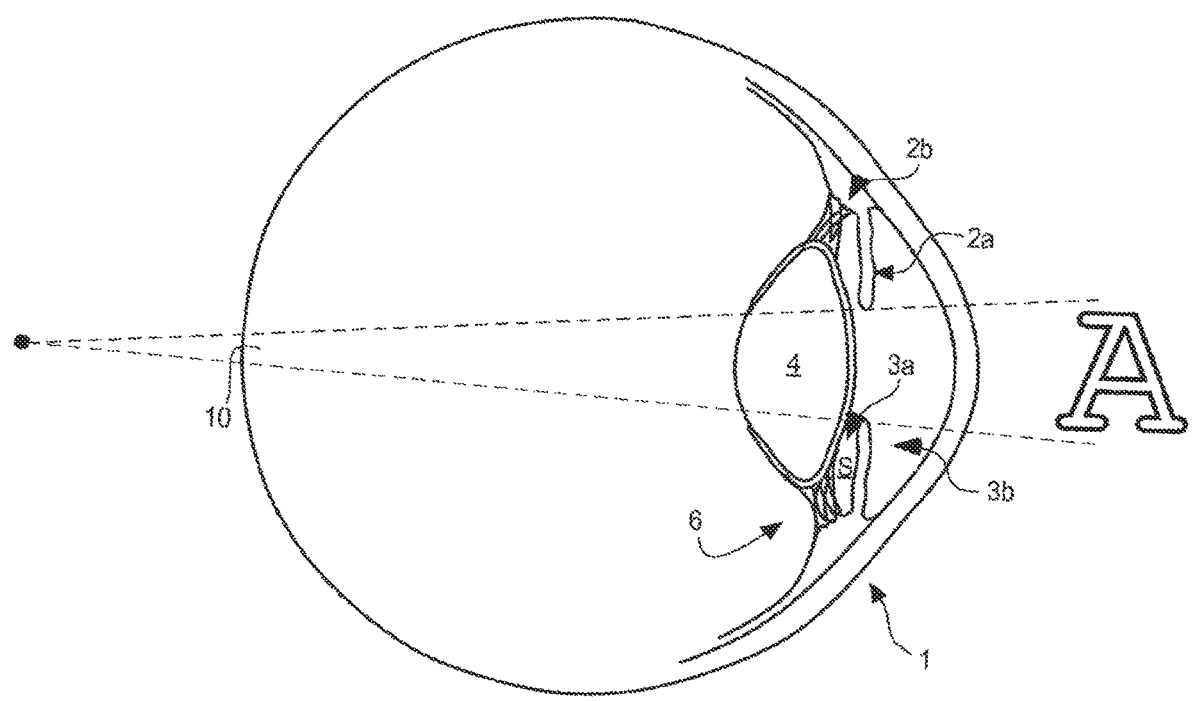
FIG. 3 is a cross-sectional side view of an eye and its main internal structures, demonstrating the rearward (relative to optimum) focal point of the eye in the visual state of hyperopia.
Figure 4:
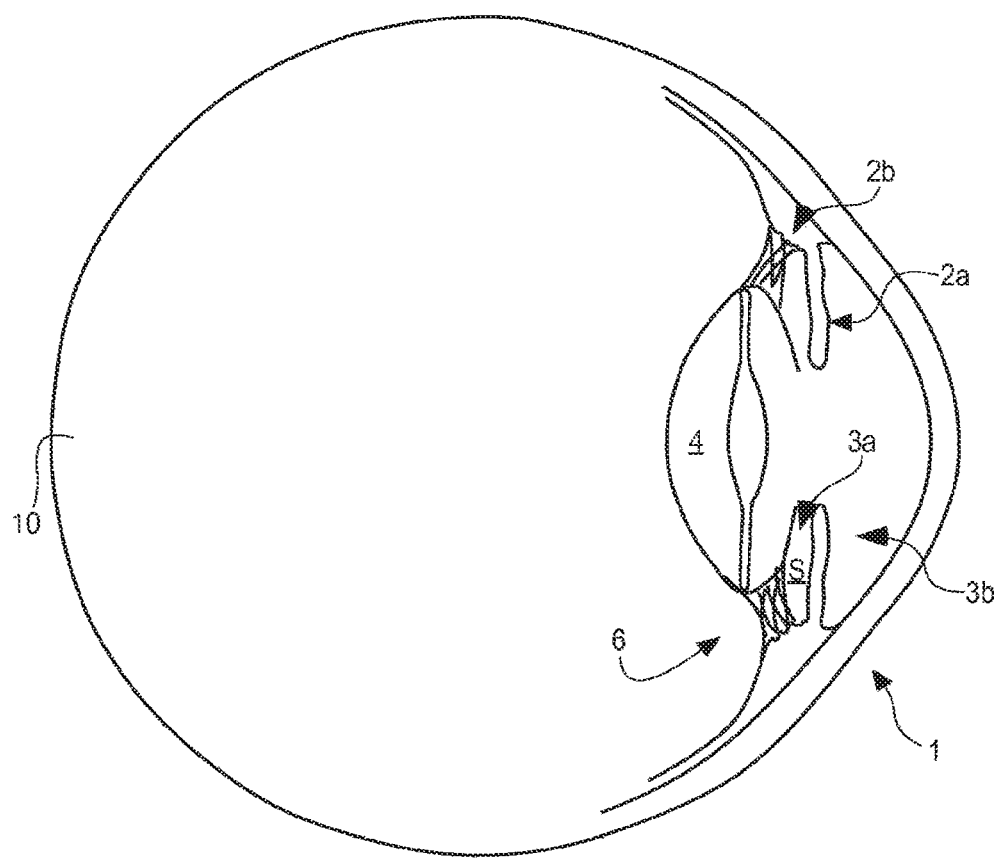
FIG. 4 is a cross-sectional side view of an eye without a natural lens and having a replacement intraocular lens positioned equatorially inside the capsular bag.
Figure 5:
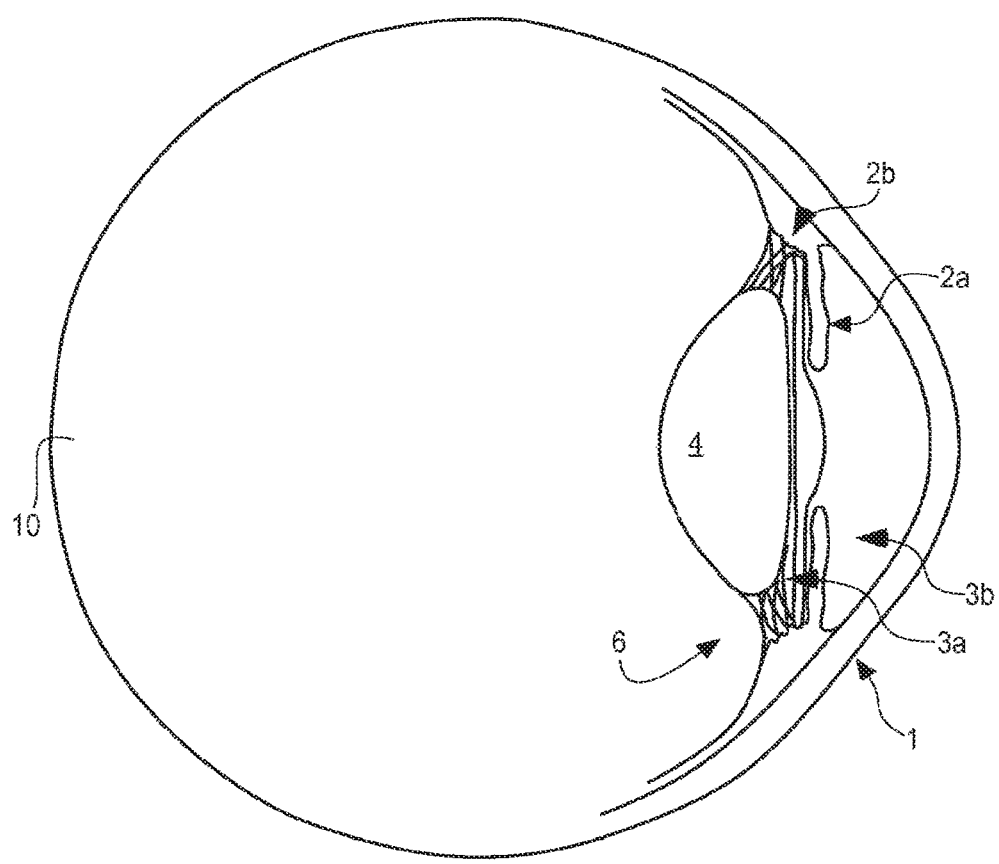
FIG. 5 is a cross-sectional side view of an eye with a phakic lens implanted in the posterior chamber.
Figure 6:
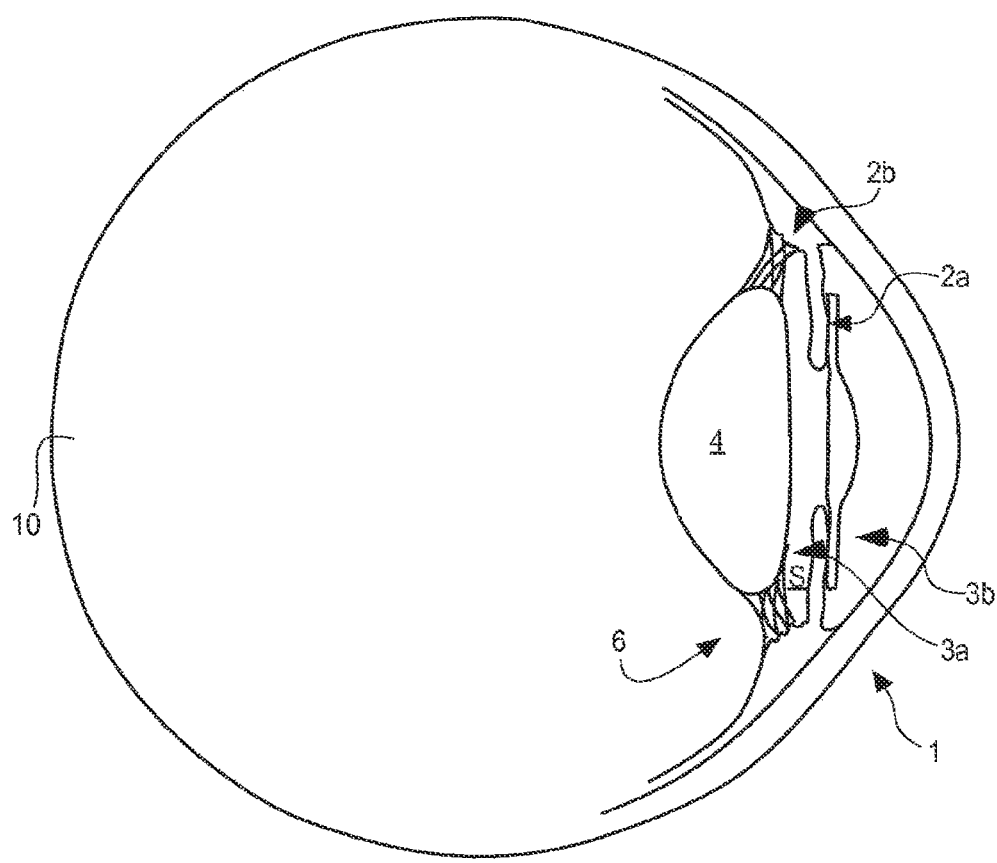
FIG. 6 is a cross-sectional side view of an eye with a phakic lens implanted in the anterior chamber.

IOL 110 is configured to be implanted in the eye as illustrated in FIGS. 4-6. When properly positioned, optical body 107 is centered in the pupil with the anterior lens face facing towards the posterior face of the cornea 1 and the posterior intraocular lens face facing towards the retina.

Figure 15:
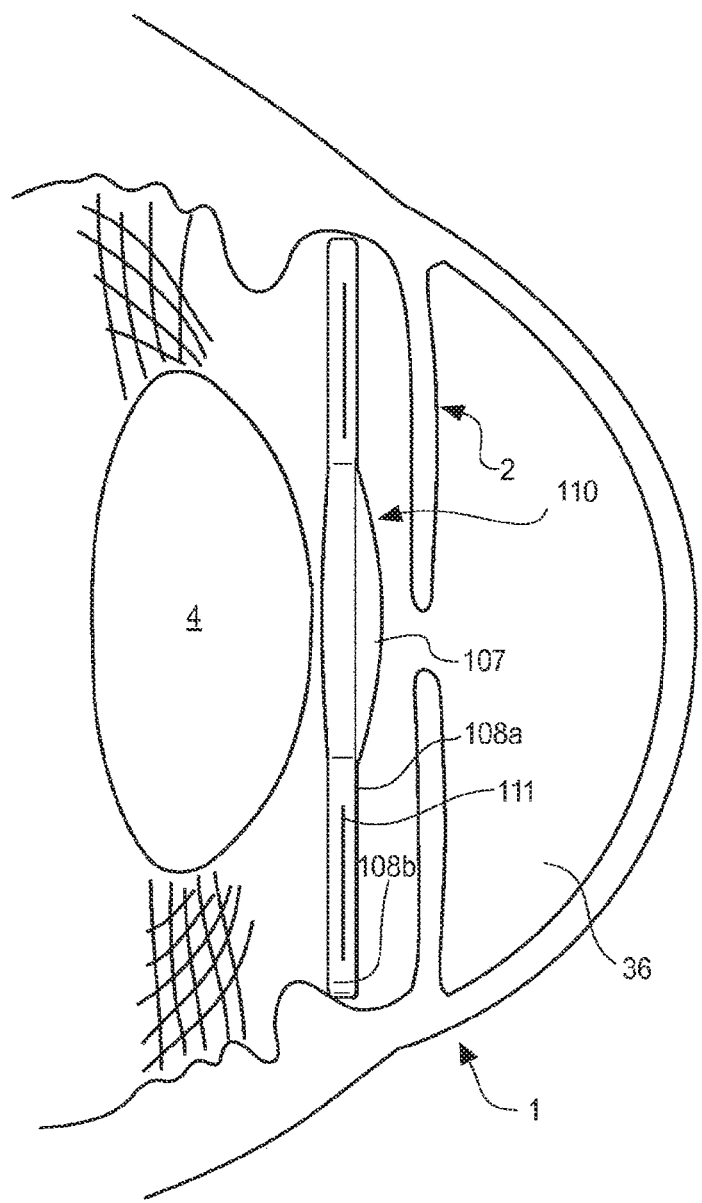
FIG. 15 is a cross-sectional schematic side view representation of a posterior-chamber-implanted phakic intraocular lens that is in contact with the natural lens.
Figure 16:
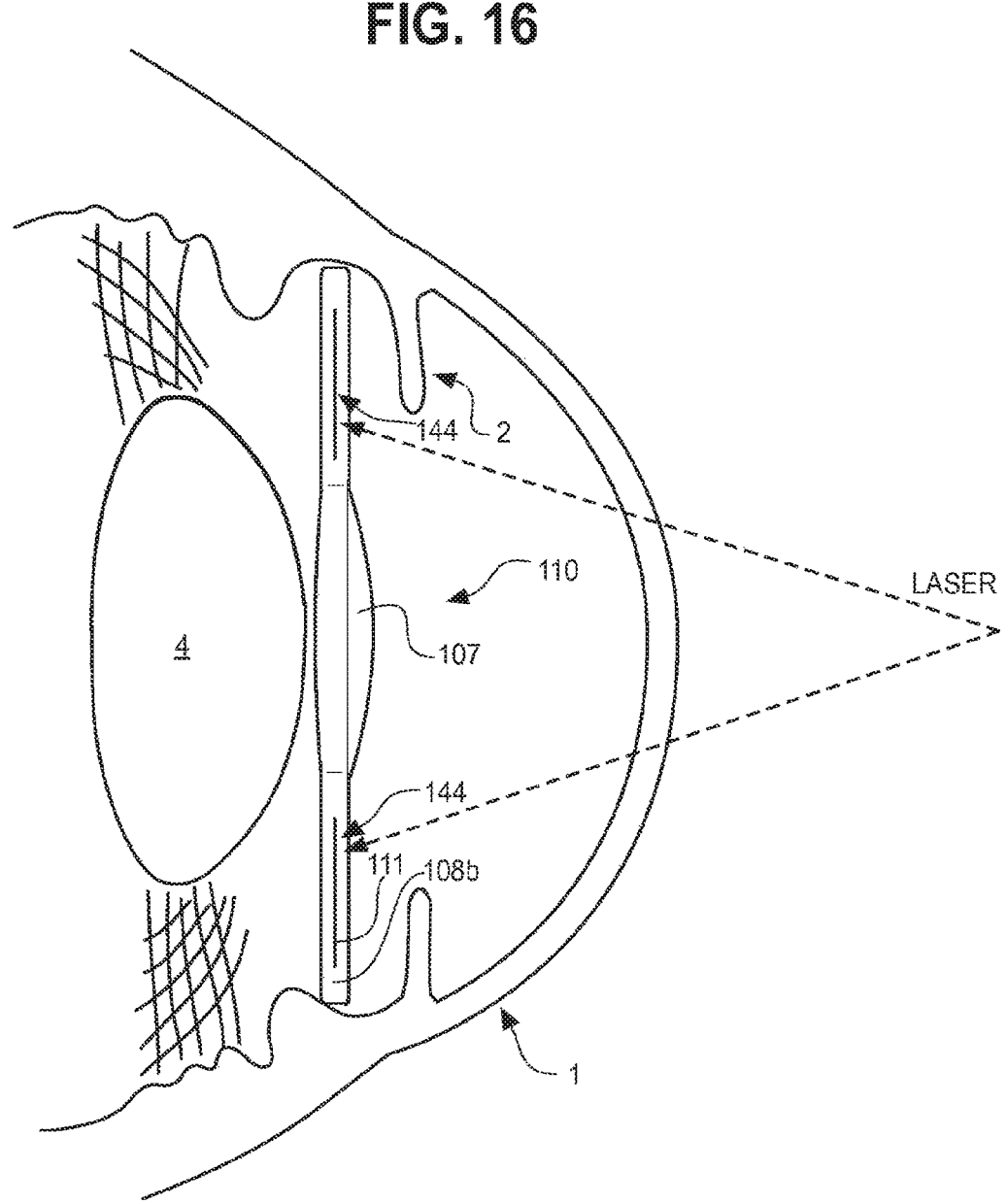
FIG. 16 is a cross-sectional side view of a eye with the iris dilated and imaginary axes that may be employed along which the laser beam may be directed to contact the shape memory alloy in a haptic-located device.
Figure 17:
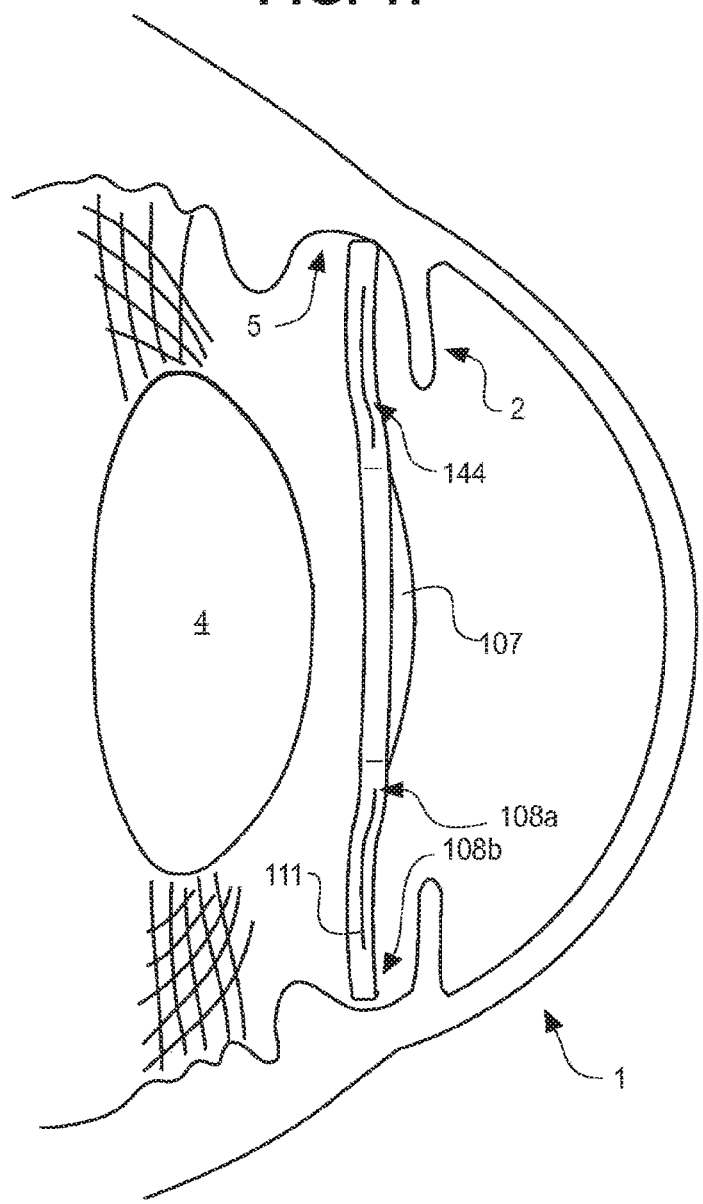
FIG. 17 is a cross-sectional side view of a posterior-chamber-implanted phakic intraocular lens having memory shape alloy haptics (containing a memory shape alloy device) bent at an angle that allow repositioning of the implanted lens further away from the natural lens to zoom out the optics of the implanted lens when an appropriate laser beam is applied to the device.

In one exemplary procedure, PIOL 110 is first inserted into the eye using standard surgical procedures. PIOL 110 (see FIG. 12) is implanted in front of the "crystalline" or natural eye lens 4 and behind the iris 2 as shown in FIG. 5. During the immediate post operative period, the PIOL's optical body 107 of PIOL 110 closes its distance with the natural lens 4, as shown in FIG. 15 causing inadequate vaulting. After the undesired condition is identified, the patient's pupil is dilated with drops (see dilation represented in FIG. 16). Some of at least one of the haptic's internal alloy shape memory devices 11 are exposed as a consequence of the dilation and are irradiated with an argon laser at specific points or segments along shape memory bars 111 with concomitant heat production. Upon reaching the transition temperature of shape memory bars 111, the bars change shape or deform. As a result, haptics 108, which contain shape memory bars 111, likewise change shape or deform. This, in turn, repositions IOL 110 to increase the distance between the natural lens and the optical body 107 of IOL 110 (FIG. 17), thus creating a proper vault or space without the need to surgically remove PIOL 110.

Figure 18:
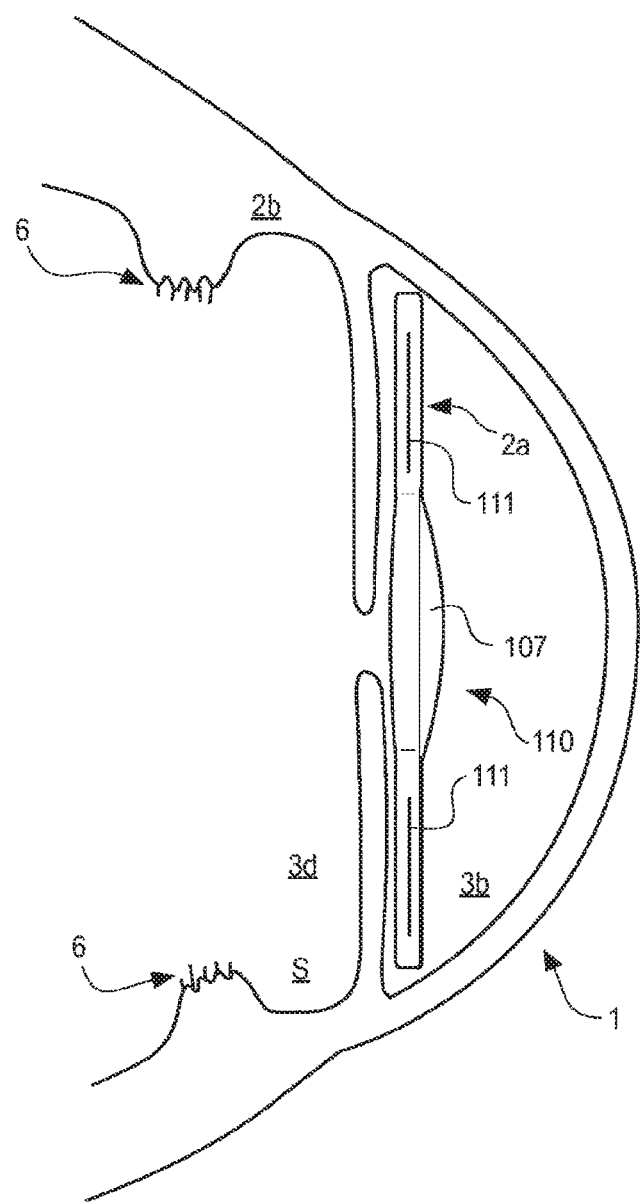
FIG. 18 is a cross-sectional side view of an IOL placed in the anterior chamber of the eye.
Figure 19:
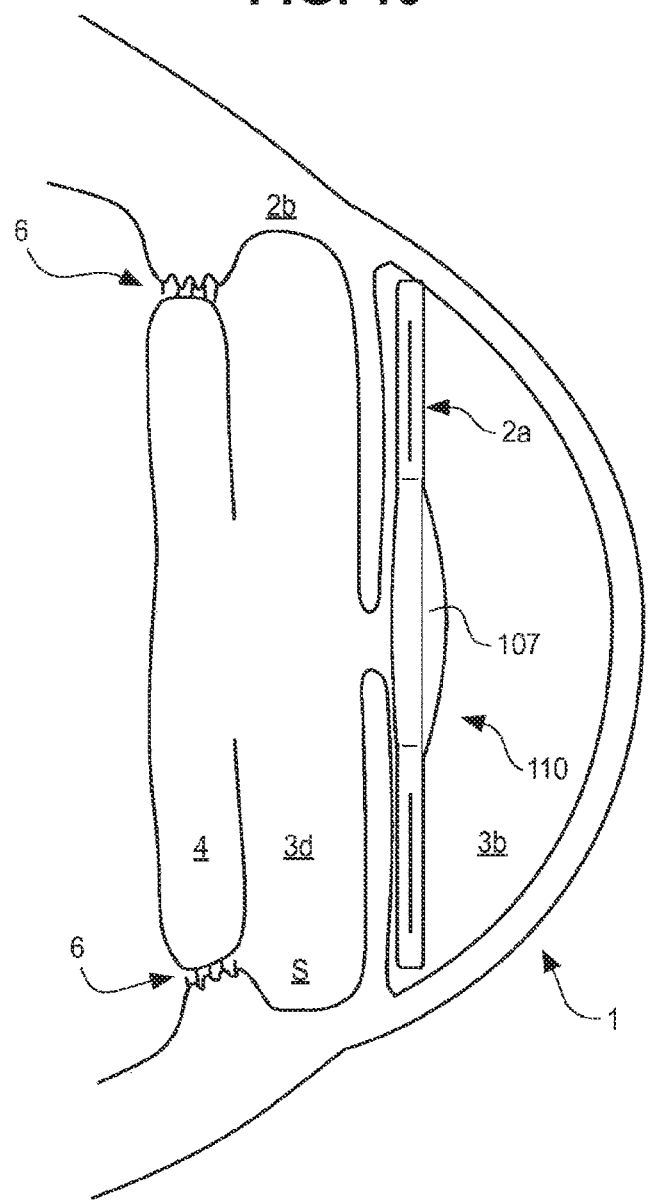
FIG. 19 is a cross-sectional side view of an IOL placed in the anterior chamber of the eye and its location with respect to the natural eye's capsular sac left intact after removal of the natural lens.

FIG. 18 shows the positioning of IOL 110 (pseudophakic) in the anterior chamber of the eye in relation to the cornea (1); central iris (2*a*); peripheral iris (2*b*); posterior chamber (3*a*); anterior chamber (3*b*); sulcus (5); ciliary zonule; and (6) in the absence of the natural lens (removed during surgery). FIG. 19 similarly shows the positioning of IOL 110 (phakic) of the present invention in the anterior chamber of the eye in relation to the cornea (1); central iris (2*a*); peripheral iris (2*b*); posterior chamber (3*a*); anterior chamber (3*b*); natural lens (4); sulcus (5); and ciliary zonule (6).

Figure 20:
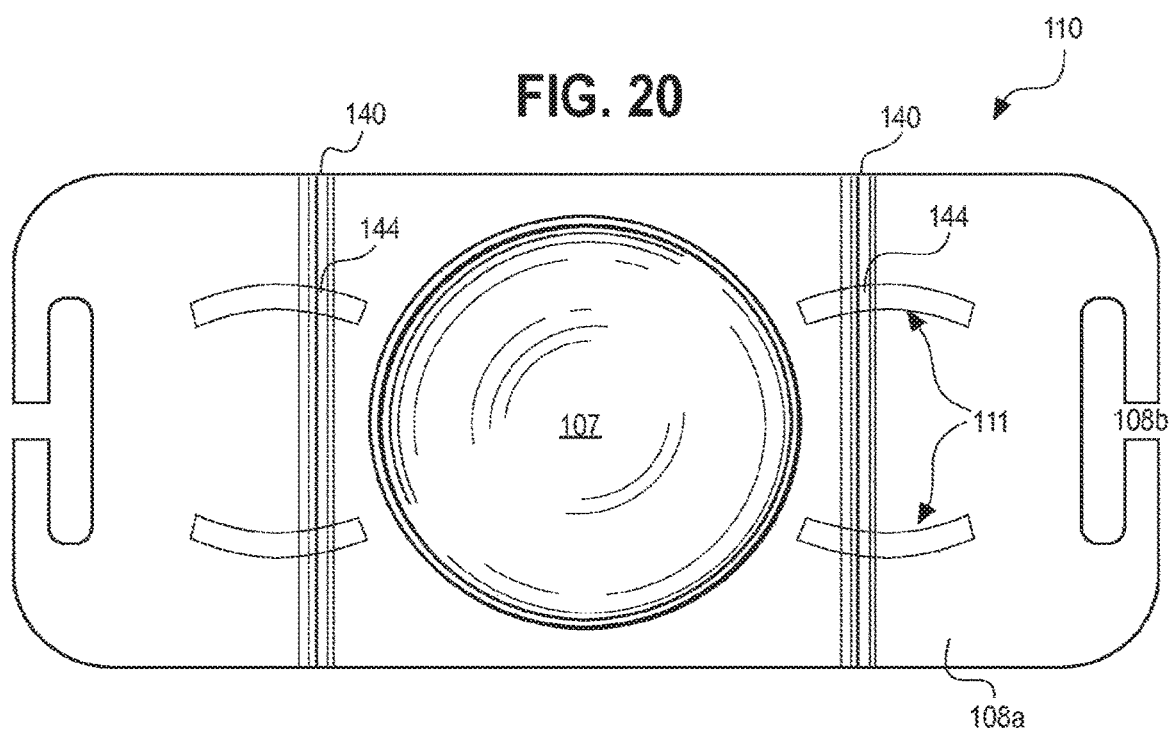
FIG. 20 is a front view of an embodiment of an intraocular lens having multiple haptics, each haptic having multiple shape memory alloy devices.
Figure 20A:
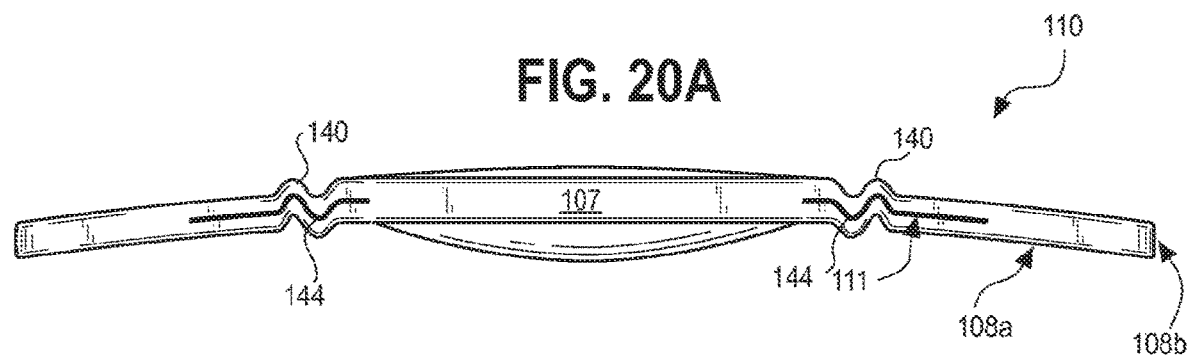
FIG. 20A is a side view of the intraocular lens of FIG. 20.
Figure 21:
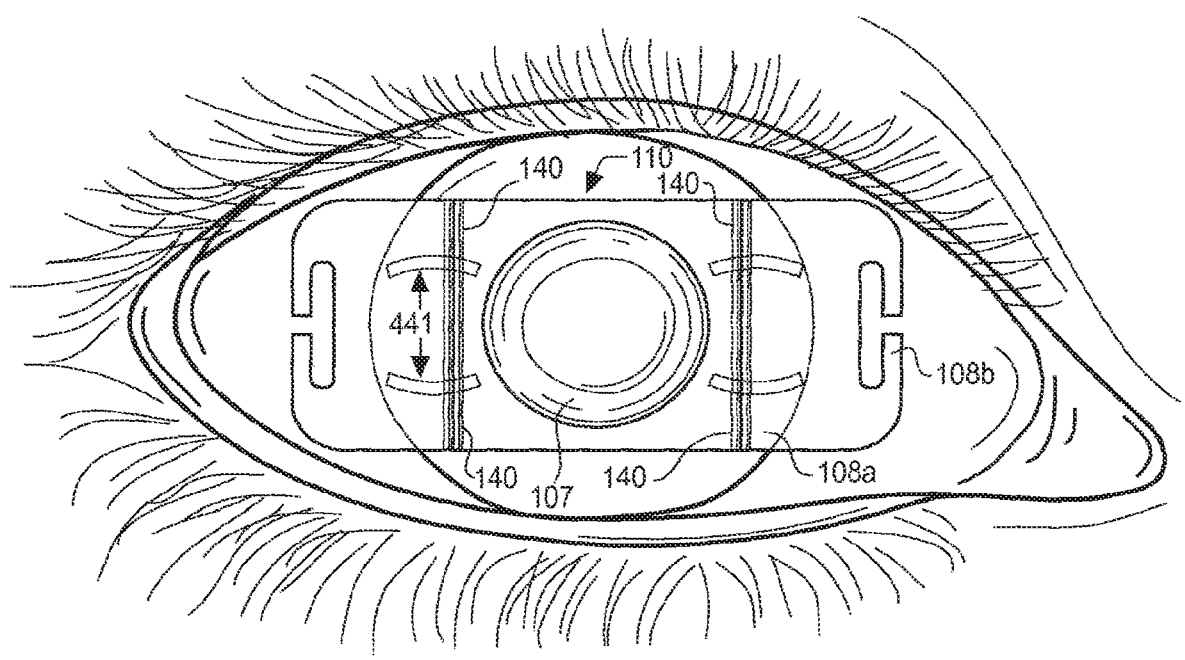
FIG. 21 is a front view of an IOL of the present invention positioned in the eye with iris dilated in preparation for adjustments to its positioning with laser irradiation.

FIG. 20 shows an IOL 110 embodiment having multiple haptics each attached to an area of lens 107 having a proximal area 108*a* of haptic 108, a distal area 108*b* of haptic 108; and shape memory bars 111. Each memory alloy device shape is deformed in a manner to provide a specific adjustment to the lens position within at least one of three dimensions associated with the lens' position in the eye. FIG. 21 shows an IOL 110 embodiment of the present invention positioned in the eye with iris dilated to expose shape memory alloy in preparation for adjustments to the IOUs positioning with laser irradiation.

In one embodiment of an IOL 110, at least one haptic 108 includes two or more shape memory bars 111. More preferably it includes two or more device memory shape alloys or at least one device memory shape alloy having multiple locations on the device to dimensionally adjust the position of the lens after the lens is implanted. Shape memory alloys are designed to alter their shape in a predetermined manner through the application of electromagnetic waves, preferably heat, preferably highly focused heat, that may be provided by use of a laser enabling a physician to specifically target where on the device heat is applied. The device preferably has multiple locations that are susceptible to the application of electromagnetic waves resulting in shape changes that affect the positioning of the lens in any of a number of directions. In this way the shape of the alloy may be manipulated to move the lens forward, back, up, down, in or out relative to the position of the natural lens or iris of the patient. The shape memory alloy is preferably designed to allow initial movements of the lens in any direction as well as revert or partially revert the lens position in situations where the lens position was initially overcorrected. This may be achieved by employing multiple hot spots on a device memory shape alloy or series of such devices where particular points in the device or devices are associated with particular movements of the lens within the implanted eye. Employing the use of highly focused electromagnetic waves, the physician can fine tune to position of the implanted lens to optimize the vision of the patient without the need for additional invasive surgery.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. An intraocular lens implant for the correction of vision comprising:
    a single flexible optical lens with a default refractive power; and
    at least one rectangular haptic attached to the single flexible optical lens;
    wherein the at least one rectangular haptic comprises at least one integral shaped memory bar (111) having a shaped memory alloy segment with a transition temperature between 50-500° C.;
    wherein the at least one rectangular haptic and the at least one integral shaped memory bar (111) are provided with a crinkled portion (144) that coincides with an expansion zone (140) of the at least one rectangular haptic being deformable in shape, holding the deformed shape while the at least one integral shaped memory bar (111) is under said transition temperature; and
    wherein the crinkled portion (144) has points associated with particular movements of the single flexible optical lens adapted to be implanted one an eye of a patient in order to allow repositioning, forward, back, up, down, in, or out movements relative to the position of a natural lens or iris of the patient;
    wherein a position of the single flexible optical lens is reverted or partially reverted through heating by a laser beam said points of the crinkled portion (144);
    wherein only once all said points have reached said transition temperature, the crinkled portion (144) returns to a forged shape.

2. The intraocular lens implant of claim 1, wherein the single flexible optical lens comprises a monofocal region.

3. The intraocular lens implant of claim 1, wherein the single flexible optical lens comprises a multifocal region.

4. The intraocular lens implant of claim 1, wherein the shaped memory alloy segment comprises nickel titanium.

5. An intraocular lens implant for the correction of vision comprising:
    a single flexible optical lens with a default refractive power; and
    at least one rectangular haptic attached to the single flexible optical lens;
    wherein the at least one rectangular haptic comprises at least one integral shaped memory bar (111) made of a shaped memory alloy segment with a transition temperature between 50-500° C., wherein the shaped memory alloy segment is a material having a plastic deformation and returns to an original forged state gradually on the basis of biasing forces and an external heating action;
    wherein the at least one rectangular haptic and the at least one integral shaped memory bar (111) are provided with a crinkled portion (144) that coincides with an expansion zone (140) of the at least one rectangular haptic being deformable in shape, holding the deformed shape while the at least one integral shaped memory bar (111) is under said transition temperature.

* * * * *